United States Patent
Wadman et al.

(10) Patent No.: US 9,914,715 B2
(45) Date of Patent: Mar. 13, 2018

(54) PROCESS FOR THE PRODUCTION OF FURAN AND ITS DERIVATIVES

(71) Applicant: SHELL OIL COMPANY, Houston, TX (US)

(72) Inventors: Sipke Hidde Wadman, Amsterdam (NL); Jean Paul Andre Marie Joseph Ghislain Lange, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/129,863

(22) PCT Filed: Mar. 26, 2015

(86) PCT No.: PCT/EP2015/056657
§ 371 (c)(1),
(2) Date: Sep. 28, 2016

(87) PCT Pub. No.: WO2015/150241
PCT Pub. Date: Oct. 8, 2015

(65) Prior Publication Data
US 2017/0137395 A1    May 18, 2017

(30) Foreign Application Priority Data
Mar. 31, 2014   (EP) .................................. 14162689

(51) Int. Cl.
*C07D 307/08*   (2006.01)
*C07D 307/36*   (2006.01)

(52) U.S. Cl.
CPC ................. *C07D 307/36* (2013.01)

(58) Field of Classification Search
CPC .................................................... C07D 307/36
(Continued)

(56) References Cited

U.S. PATENT DOCUMENTS 5,905,159 A * 5/1999 Fischer ................. C07C 29/132
549/429

FOREIGN PATENT DOCUMENTS

| CN | 101967133 | 2/2011 |
| CN | 102000569 A | 4/2011 |

(Continued)

OTHER PUBLICATIONS

Dunlop, A.P. et al.: The Furans, "Furan and its Homologs", pp. 31-32, 1953.
(Continued)

*Primary Examiner* — T. Victor Oh

(57) ABSTRACT

The present invention provides a process for the production of furan, said process comprising the steps of: i) contacting furfural with a decarbonylation catalyst in a decarbonylation reactor to produce a gaseous decarbonylation reaction product stream comprising furan and carbon monoxide; ii) contacting said gaseous decarbonylation reaction product stream with a solvent stream comprising furfural; iii) absorbing at least a portion of the furan present in the gaseous decarbonylation reaction product stream into the solvent stream to provide a furan-containing solvent stream and a gaseous stream comprising carbon monoxide; iv) separating the furan from the furan containing solvent stream by distillation to provide a first furan stream; and v) using at least a portion of the remaining solvent stream comprising furfural as at least a portion of the furfural provided to the decarbonylation reactor.

4 Claims, 2 Drawing Sheets

(58) Field of Classification Search
USPC .......................................................... 549/505
See application file for complete search history.

(56) References Cited

FOREIGN PATENT DOCUMENTS

| | | | |
|---|---|---|---|
| CN | 103084168 A | | 5/2013 |
| DE | 102009047503 A1 | | 7/2010 |
| EP | 0096913 A1 | | 12/1983 |
| JP | 2013159594 | * | 8/2013 |
| WO | 02022593 | | 9/2001 |

OTHER PUBLICATIONS

Hoydonckx, H.E, et al. Ullmann's, "Furfural and Derivatives", vol. 16, pp. 287-313.
Lange, J-P., et al.: CHEMSUSCHEM 2012, "Furfural—A Promising Platform for Lignocellulosic Biofuels", DOI 10.1002/esse. 201100648, 5, pp. 150-166.
Watson, James M.: IND. ENG. CHEM. PROD. RES. DEVELOP. "Butane-1,4-diol from Hydrolytic Reduction of Furan", vol. 12, No. 4, 1973, pp. 310-311.
Zeitsch, Karl J.: Sugar Series, 13, "The chemistry and technology of furfural and its many by-products", Elsevier, 2000, pp. 150-155.
International Search Report dated May 8, 2015 of PCT/EP2015/056657 filed Mar. 26, 2015.

* cited by examiner

PROCESS FOR THE PRODUCTION OF FURAN AND ITS DERIVATIVES

PRIORITY CLAIM

The present application is a National Stage (§ 371) application of PCT/EP2015/056657, filed 26 Mar. 2015, which claims priority from European patent Application 14162689.5 filed 31 Mar. 2014, each of which are hereby incorporated by reference in their entirety.

FIELD OF THE INVENTION

The present invention relates to a process for the production of furan and its derivatives.

BACKGROUND OF THE INVENTION

Furan and its derivatives are useful precursors for industrial chemicals in the area of, for example, pharmaceuticals, herbicides and polymers. Furan can readily be converted into tetrahydrofuran (THF) and 1,4-butanediol (1,4-BDO), which are valuable chemicals used industrially as solvents and in the production of elastic fibres such as elastane/spandex, polybutyrate terephthalate and derivatives of gamma butyrolactone.

These chemicals are usually produced industrially via a number of routes from petrochemical feedstocks, obtainable from fossil fuels. One industrial route for the production of 1,4-BDO requires the reaction of acetylene with two equivalents of formaldehyde followed by hydrogenation of the resultant 1,4-butynediol to form 1,4-butanediol. In an alternative process, propylene oxide is converted to allyl alcohol. The allyl alcohol is then hydroformylated to form 4-hydroxybutyraldehyde, which may be hydrogenated to form 1,4-butanediol. Other traditional routes use butadiene, allyl acetate or succinic acid as starting materials.

1,4-butanediol may also be produced as a side-product in a method for making tetrahydrofuran (THF) by oxidizing n-butane to crude maleic anhydride followed by catalytic hydrogenation.

In recent years, increased efforts have focused on producing chemicals, including furan and its derivatives such as 1,4-BDO and THF, from renewable feedstocks, such as sugar-based materials.

A method for obtaining furan from non-fossil fuel based sources involves the decarbonylation of furfural. Examples of reaction processes for achieving this and the subsequent conversion of the furan into its derivatives can be found in Hoydonck, H. E., Van Rhijn, W. M., Van Rhijn, W., De Vos, D. E. & Jacobs, P. A. (2012) Furfural and Derivatives, in Ulmann's Encyclopedia of Industrial Chemistry (volume 16, pp 285-313), Wiley-VCH Verlag GmBH & Co. KGaA, Weinheim; Dunlop, A. P. and Peters, F. N., in The Furans Reinhold Publ. Co, 1953; K. J. Zeitsch, in "The Chemistry and Technology of Furfural and its Many By-products" Sugar Series 13, Elsevier, 2000; Lange, J-P, van der Heide, E, van Buijtenen, J., and Price, R.; Furfural—A Promising Platform for Lignocellulosic Biofuels; ChemSusChem 2012, 5, 150-166 and Watson, J. M., Ind. Eng. Chem. Prod. Res. Develop., 1973, 12(4), 310. Furfural may be obtained from hemicellulose via acid hydrolysis in the liquid phase as well as in the gas phase as described in WO 2002/22593 and WO 2012/041990.

The product stream from a reaction process including the decarbonylation of furfural will contain furan, carbon monoxide, hydrogen and other by-products. Furan can be recovered from the dilute gas stream by condensation after considerable compression and cooling of the stream comprising furan, CO and $H_2$, for example to greater than 1.5 MPa and less than 20° C. However, due to the low boiling point of furan (31.3° C.), it is difficult to reclaim essentially all furan from this gas stream. Deep removal of carbon monoxide from the furan stream is also critical as carbon monoxide can act as a poison to catalysts used in subsequent reactions to convert the furan into THF and 1,4-BDO.

CN 101967133 describes a process for producing furan by decarbonylation of furfural, wherein after the decarbonylation reaction, the resultant gaseous mixture is condensed and a liquid furan product is collected. Further furan is then recovered from the remaining gas phase by absorption with a solvent. Preferred solvents are furfural, benzene, toluene and xylene. These solvents can be recycled for re-use in the absorption step.

JP 2013-159594A discloses a method for producing furan, wherein furfural is supplied to a reactor as a raw material. Furan is then produced by performing a decarbonylation reaction in the presence of a catalyst. A mixed gas containing the product furan as a main component is extracted from an outlet of the reactor. Said mixed gas is then brought into contact with a solvent so as to separate furan from the mixed gas, wherein furfural is used as the solvent. After separation of the furfural solvent, it is recycled for re-use.

It would be advantageous to provide a more efficient and integrated method for the production of furan from furfural in which the furan may be separated from undesirable by-products made in its production without significant losses of useful materials and without contamination with undesirable by-products such as carbon monoxide.

SUMMARY OF THE INVENTION

Accordingly, the present invention provides a process for the production of furan, said process comprising the steps of:
i) contacting furfural with a decarbonylation catalyst in a decarbonylation reactor to produce a gaseous decarbonylation reaction product stream comprising furan and carbon monoxide;
ii) contacting said gaseous decarbonylation reaction product stream with a solvent stream comprising furfural;
iii) absorbing at least a portion of the furan present in the gaseous decarbonylation reaction product stream into the solvent stream to provide a furan-containing solvent stream and a gaseous stream comprising carbon monoxide;
iv) separating the furan from the furan containing solvent stream by distillation to provide a first furan stream; and
v) using at least a portion of the remaining solvent stream comprising furfural as at least a portion of the furfural provided to the decarbonylation reactor.

DETAILED DESCRIPTION OF THE INVENTION

Figure 1:
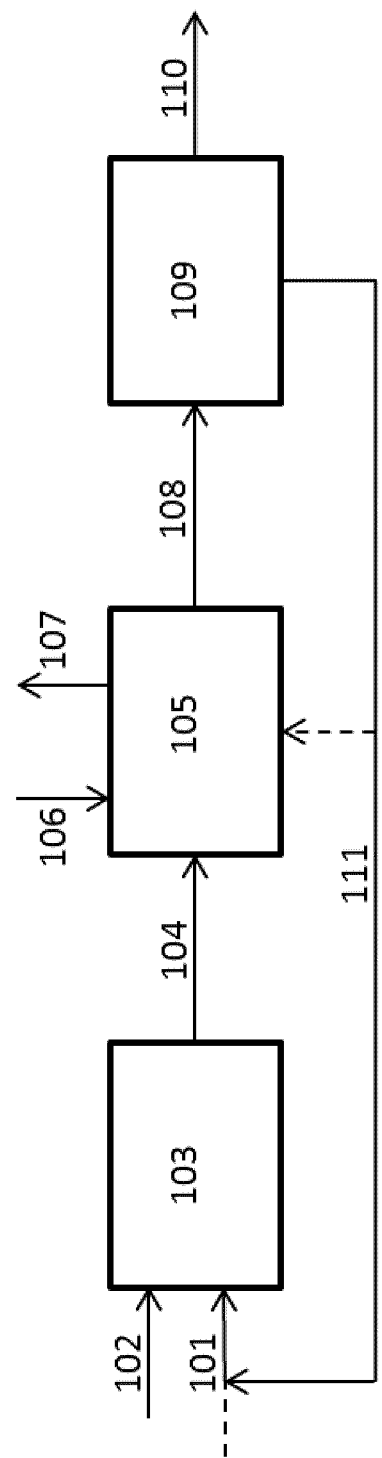
FIGS. 1 and 2 are schematic diagrams of exemplary, but non-limiting, embodiments of the process described herein.

The present inventors have surprisingly found that furan may be separated from a decarbonylation reaction product stream comprising furan and carbon monoxide by contacting said reaction product stream with a solvent stream comprising furfural and absorbing the furan into said solvent stream. After separation of the furan and furfural, the furfural may be used as at least a portion of the source of furfural for the decarbonylation reaction. This allows a reduction in distillation duty as complete separation of the furan from the furfural is unnecessary. Any furan remaining in the furfural will be recycled via the decarbonylation reactor and not be lost from the process.

The furan is produced from furfural by a decarbonylation reaction in which the furfural is contacted with a decarbonylation catalyst in a decarbonylation reactor, preferably in the presence of hydrogen. The nature of the decarbonylation catalyst is not critical to the present invention and any catalyst suitable for the decarbonylation of furfural may be used.

Exemplary suitable decarbonylation catalysts include heterogeneous, supported catalysts. These decarbonylation catalysts suitably contains a metal selected from the group consisting of iron (Fe), ruthenium (Ru), osmium (Os), cobalt (Co), rhodium (Rh), iridium (Ir), nickel (Ni), palladium (Pd), platinum (Pt) and mixtures thereof.

Preferably, the metal in the decarbonylation catalyst is selected from the group consisting of Rh, Ir, Pd, Pt and mixtures thereof. More preferably, the metal in the decarbonylation catalyst is selected from the group consisting of Pd, Pt and a mixture of Pd and Pt. Even more preferably, the metal in the decarbonylation catalyst is Pd or Pt. Most preferably, the metal in the decarbonylation catalyst is Pd.

The total amount of the metal or metals selected from the group consisting of Fe, Ru, Os, Co, Rh, Ir, Ni, Pd, Pt and mixtures thereof may vary within wide ranges, and may be of from 0.01 to 20 wt %, 0.1 to 10 wt % or 0.5 to 5 wt % on the basis of the total weight of the catalyst. Preferably, the total amount of said metal or metals is at least 0.01 wt %, more preferably at least 0.05 wt %, more preferably at least 0.1 wt %, more preferably at least 0.3 wt %, more preferably at least 0.5 wt %, most preferably at least 0.7 wt %. Further, preferably, the total amount of said metal or metals is at most 20 wt %, more preferably at most 15 wt %, more preferably at most 10 wt %, more preferably at most 8 wt %, more preferably at most 5 wt %, most preferably at most 3 wt %.

Further to the above-mentioned metal or metals, the decarbonylation catalyst used in the process of the present invention may contain one or more additional metals, for example promoter metals. Suitable examples of such additional metals are alkali metals and/or alkaline earth metals. Preferably, the alkali metal is selected from the group consisting of sodium, potassium, rubidium and cesium. More preferably, the alkali metal is potassium.

The total amount of said additional metal or metals may vary within wide ranges, and may be of from 0.1 to 25 wt %, 0.5 to 15 wt % or 1 to 10 wt % on the basis of the total weight of the catalyst.

The nature of the support for the catalyst used in the process of the present invention is not essential. Said support may comprise carbon or one or more oxides selected from the group consisting of silica, alumina, barium sulfate, titanium dioxide, zirconium dioxide, magnesium silicate, diatomaceous earth and silica gel. In case the support comprises carbon, it may comprise, for example, activated carbon or carbon fibres.

During the decarbonylation step of the process of the present invention, the furfural may be contacted with the catalyst at a temperature in the range of from 100 to 450° C., preferably in the range of from 100 to 350° C., more preferably in the range of from 200 to 350° C., most preferably in the range of from 200 to 300° C., as mentioned above. The pressure during the furfural decarbonylation may be in the range of from 0.1 to 10 MPa, suitably 0.2 to 3 MPa, more suitably 0.3 to 1.5 MPa.

The decarbonylation step may be carried out in the liquid phase or gas phase. Preferably, it is carried out in the gas phase. If hydrogen is present, the molar ratio of hydrogen:furfural is preferably at least 0.1:1, more preferably at least 0.5:1. The molar ratio of hydrogen:furfural is preferably at most 100:1, more preferably at most 10:1, even more preferably at most 2:1.

As well as hydrogen, other gases may be provided to the decarbonylation step as a gas feed stream and said additional gas or gases may be selected from the group consisting of the noble gases, nitrogen, carbon monoxide, carbon dioxide, methane and steam. A suitable noble gas is argon. Preferably, if one or more additional gases are used, said gas feed stream comprises hydrogen and the additional gas or gases, for example nitrogen, in a volume ratio which is greater than 0.01:1 (hydrogen:additional gas or gases), more preferably greater than 0.1:1, more preferably greater than 1:1, more preferably greater than 5:1, more preferably greater than 10:1, more preferably greater than 50:1, more preferably greater than 100:1 and even more preferably greater than 1000:1.

Further, the hydrogen gas is suitably fed to the decarbonylation step at a rate of 0.01 to 100 Nl/g/h (normal liter per gram of catalyst per hour), preferably 0.1 to 10 Nl/g/h, more preferably 0.5 to 2 Nl/g/h. Further, the furfural may be fed at a rate of from 0.1 to 100 g/g/h (gram per gram of catalyst per hour), preferably 0.5 to 10 g/g/h.

The decarbonylation reaction product stream leaving the reactor in which the decarbonylation step occurs is gaseous. This decarbonylation reaction product stream is optionally subjected to compression and/or cooling. No compression may be applied. However, if compression occurs, the decarbonylation reaction product stream is suitably compressed to at most 5 MPa, preferably at most 2 MPa, more preferably at most 1 MPa, even more preferably at most 0.5 MPa. No cooling may be applied. However, if cooling occurs, the decarbonylation reaction product stream is suitably cooled to a temperature no more than 150° C., preferably no more than 100° C., more preferably no more than 50° C., most preferably no more than 25° C. Such levels of cooling may be achieved using air or water cooling in most parts of the world. In another embodiment, more severe cooling may be carried out in order to chill the decarbonylation reaction product stream to temperatures of 0° C. or less, such as temperatures less than −10° C. or temperatures less than −20° C.

If compression and/or cooling is/are applied to the decarbonylation reaction product stream, condensation of liquid material comprising furan may occur. This liquid material may be separated from the decarbonylation reaction product stream and, optionally, recombined with a furan-containing stream after the absorption step.

After any compression and/or cooling and/or separation of condensed material, the decarbonylation reaction product stream is then contacted with a liquid solvent stream comprising furfural.

The solvent stream comprising furfural is contacted with the gaseous decarbonylation reaction product stream in any suitable method for gas/liquid contacting. The contacting can be performed in co-, counter- or cross-flow. Exemplary suitable methods for effecting said contact include, but are not limited to, bubbling the gas stream through the liquid solvent stream, spraying the liquid solvent stream into a the gas stream or flowing the gas and liquid streams over gas/liquid contacting devices. For instance, the gas/liquid contacting devices can consist of monolytic structures such as distillation trays, corrugated plates or grids, static mixers. However, it can also consist of structured or random beds of porous or non-porous structures such as beads, rings, cylinders, saddles and the likes.

The solvent stream comprising furfural may be brought into contact with the decarbonylation reaction product stream once or multiple times in order to absorb the furan into the solvent stream. In an alternative embodiment of the invention, the solvent stream comprising furfural may comprise a number of separate solvent streams comprising furfural that are contacted individually with the gaseous decarbonylation reaction product stream and then combined.

Suitably the solvent stream contains furfural such that the molar ratio of furfural:furan is at least 0.1:1, preferably at least 0.2:1, more preferably at least 0.5:1. Further, the solvent stream suitably contains furfural such that the molar ratio of furfural:furan is at most 50:1, preferably at most 20:1, more preferably at most 10:1.

At least a portion of the furan in the decarbonylation reaction product stream is absorbed into the solvent stream comprising furfural to provide a furan-containing solvent stream. Preferably at least 90 wt %, more preferably at least 95 wt %, even more preferably at least 99 wt %, even more preferably at least 99.5 wt %, most preferably at least 99.9 wt % of the furan in the decarbonylation reaction product stream is absorbed into the solvent stream comprising furfural to produce a furan-containing solvent stream.

After absorption of the furan into the solvent stream comprising furfural, the remaining gaseous stream comprises hydrogen and carbon monoxide. It is likely that this stream will also contain some furan and solvent. This stream may be recycled, partially recycled, used as fuel or supplied to a different reaction, e.g. a water-gas shift reaction.

In a preferred embodiment of the present invention, the furan is separated from the furan-containing solvent stream by distillation to provide a furan stream. This may be achieved without substantial loss of the furan. Further, it is preferable that the furan can be obtained from the furan-containing solvent stream with minimal contamination by the solvent. If the furan-containing solvent stream is subjected to a distillation step in which the furan is separated from the furfural, the distillation may be carried out under any suitable conditions.

After distilling off the furan, at least a portion of the remaining solvent stream comprising furfural is used as at least a portion of the source of furfural for the decarbonylation reaction. As an alternative, a portion of the remaining solvent stream comprising furfural may be used as the source of furfural for the decarbonylation reaction and a portion of the remaining solvent stream comprising furfural may be recycled for re-use as the solvent stream. These options both have the advantage that it would be unnecessary to entirely separate the furan from the remaining solvent stream comprising furfural as any furan still remaining in this stream would remain in the process. This would reduce the distillation duty at this stage.

The furan stream separated from the furan-containing solvent stream, or the furan-containing solvent stream in the embodiment of the invention wherein the solvent used is a material which is compatible with, present or formed in a later transformation of the furan, may be subsequently contacted with hydrogen in the presence of a hydrogenation catalyst in order to produce a hydrogenation reaction product stream comprising THF and/or 1,4-BDO.

Any suitable hydrogenation catalyst and conditions may be applied in this step of the process. Suitable catalysts include, but are not limited to group 8-11 metals supported on standard supports and unsupported 'skeletal/Raney' metals.

The hydrogenation reaction can proceed in the gas or the liquid phase. Suitable conditions for the production of mainly THF include the use of an inert or moderately polar solvent such as a hydrocarbon or oxygenate, a temperature in the range of from 50 to 250° C., a pressure of from 0.1 to 10 MPa and a $H_2$:furan molar ratio in the range of from 0.2:1 to 100:1, preferably in the range of from 0.2:1 to 10:1.

Suitable conditions for the production of a mixture of BDO and THF include co-feeding water as a gas or liquid at a water:furan molar ratio in the range of from 0.2:1 to 100:1. In this embodiment, further suitable conditions include the use of a solvent comprising water and/or hydrocarbon or oxygenates, preferably the reaction product (THF) or eventually by-products, a temperature in the range of from 100 to 350° C., preferably 150 to 250° C., a pressure of from 0.1 to 15 MPa and a $H_2$:furan molar ratio in the range of from 0.2:1 to 100:1, preferably in the range of from 2:1 to 10:1.

The hydrogenation reaction product stream will also comprise hydrogen and by-products from the hydrogenation reaction. These will be separated from the THF, NBA and/or 1,4-BDO. The resultant post-separation hydrogen-containing stream is at a slightly low pressure and would need to be moderately re-compressed for re-use in the hydrogenation reaction. Preferably, a bleed stream is removed from this stream in order to prevent build-up of contaminants.

There may remain some carbon monoxide in the furan stream separated from the furan-containing solvent stream. It is preferred that this is removed before the furan stream is contacted with hydrogen in the presence of a hydrogenation catalyst as a number of hydrogenation catalysts are sensitive to the presence of carbon monoxide. Any method for removing any carbon monoxide present in this furan stream is suitable for this process. However, in a further embodiment of the invention, the furan stream is contacted with a gaseous stream comprising hydrogen and any carbon monoxide present is removed from the furan into said gaseous stream. In a preferred embodiment of the invention, the gaseous stream comprising hydrogen is a process stream already present in the process. In a particularly preferred embodiment of the present invention, the gaseous stream comprising hydrogen is formed from at least a portion of the post-separation hydrogen-containing stream, more preferably the bleed stream is used. It is even more preferred that this gaseous stream comprising hydrogen, after contacting the furan stream, is provided to the decarbonylation reactor as a source of hydrogen.

DETAILED DESCRIPTION OF THE DRAWINGS

The invention will now be further illustrated with reference to the non-limiting embodiments shown in the drawings. In the drawings, the first numeral of each reference number refers to the Figure number, e.g. 1XX for FIG. 1 and 2XX for FIG. 2. The remaining figures relate to the individual features within the Figures. The same number is used to refer to the same feature in each Figure. Therefore, 107 refers to the same feature in FIG. 1 as 207 refers to in FIG. 2.

In a preferred, but non-limiting, embodiment of the invention illustrated in FIG. 1, furfural 101 and hydrogen 102 are provided to a decarbonylation reactor 103 in which is contained a decarbonylation catalyst. The resultant decarbonylation reaction product stream 104 is contacted with a solvent stream comprising furfural 106 in a vessel 105 to provide a furan-containing solvent stream 108. Hydrogen and carbon monoxide are removed as a gaseous stream 107. The furan-containing solvent stream 108 is subjected to distillation in a distillation column 109, providing a furan stream 110 and separated furfural 111. At least a portion of the separated furfural 111 is provided to the decarbonylation reactor 103 as the source of furfural. Optionally, some furfural may be recycled to the absorber. In this embodiment, fresh supply of furfural 101 would then be reduced or removed entirely.

Figure 2:
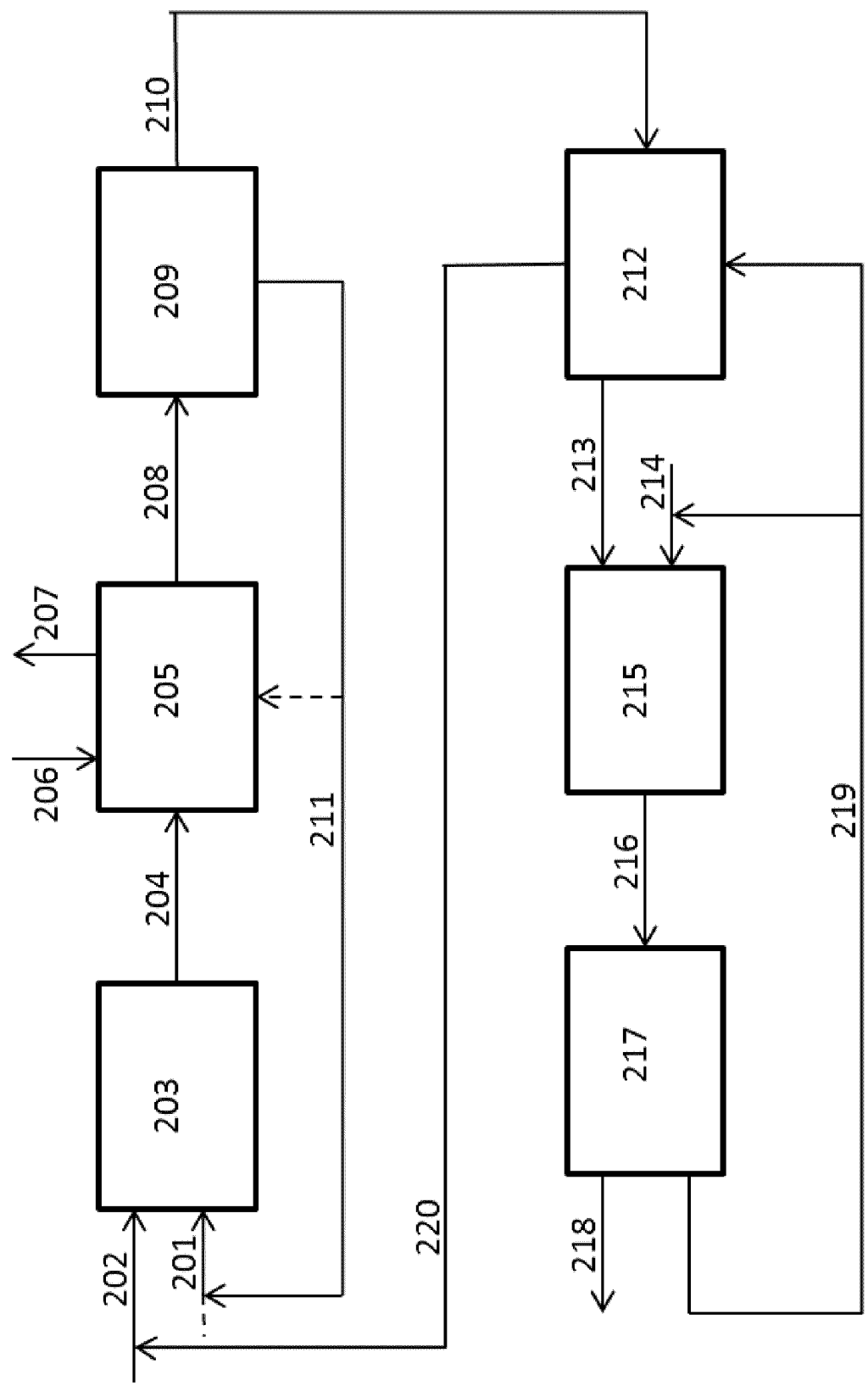

In a further particularly preferred, but non-limiting, embodiment of the invention illustrated in FIG. 2, the furan stream 210 is contacted with a gaseous stream comprising hydrogen 219 in a vessel 212 and carbon monoxide present in the furan stream 210 is removed into the gaseous stream comprising hydrogen. The resultant (CO-depleted) furan stream 213 is contacted with hydrogen 214 in a hydrogenation reactor 215 containing a hydrogenation catalyst.

The resultant hydrogenation reaction product stream 216 is separated in a column 217 to provide a product stream 218 containing 1,4-BDO and/or THF and the resultant post-separation hydrogen-containing stream 219, a portion of which is then recycled for use in removing carbon monoxide from the furan stream and the remainder can be recycled to provide hydrogen for the hydrogenation reaction.

EXAMPLES

Example 1 (Comparative)

A process line-up was developed in ASPEN, using a fit for purpose thermodynamic data deck. The product stream ex-decarbonylation reactor consisted of 98 kmol/h furan, 2 kmol/h furfural, 18 kmol/h H2 and 98 kmol/h CO, at 5 barA and 50° C. Two stage compression of this stream to 15 and 40 barA, respectively, with cooling to 10° C. resulted in the condensation of furan and furfural. After separation of the liquid streams, the gaseous stream contains 2.2 kmol/h furan and $1.2 \times 10^{-7}$ kmol/h of furfural. Accordingly, 2.2 mol % of the furan is lost in the gas phase.

Example 2 (of the Invention)

The process line-up described in example 1 was modified to contain a single stage compression, to 15 barA with cooling to 50° C. After separation from the condensate, the gaseous stream contains 20 kmol/h furan. This gas stream is then contacted with 100 kmol/h of furfural at 40° C. in a counter current extractor at 50° C. and 15 barA. The gas stream ex-contactor contains $4 \times 10^{-5}$ kmol/h of furan and 0.08 kmol/h of furfural. The liquid furfural/furan stream is combined with the condensate stream and the furan is isolated by distillation. Accordingly, 0.4 ppm of the furan is lost in the gas phase.

That which is claimed is:

1. A process for the production of furan, said process comprising the steps of:
    i) contacting furfural with a decarbonylation catalyst in a decarbonylation reactor to produce a gaseous decarbonylation reaction product stream comprising furan and carbon monoxide;
    ii) contacting said gaseous decarbonylation reaction product stream with a solvent stream comprising furfural;
    iii) absorbing at least a portion of the furan present in the gaseous decarbonylation reaction product stream into the solvent stream to provide a furan-containing solvent stream and a gaseous stream comprising carbon monoxide;
    iv) separating the furan from the furan containing solvent stream by distillation to provide a first furan stream; and
    v) using at least a portion of the remaining solvent stream comprising furfural as at least a portion of the furfural provided to the decarbonylation reactor.

2. A process according to claim 1, wherein the decarbonylation reaction stream is subjected to cooling and/or compression before being contacted with a solvent stream in step ii) and any liquid condensed is separated.

3. A process according to claim 1, wherein the process further comprises the steps of:
    i) contacting said first furan stream with a CO-lean first gaseous stream; and
    ii) stripping at least a portion of any carbon monoxide remaining in the first furan stream into the first gaseous stream to produce a liquid second furan stream comprising less carbon monoxide than the first furan stream and a CO-enriched second gaseous stream.

4. A process according to claim 3 wherein the process further comprises the steps of:
    i) contacting the second furan stream with hydrogen in the presence of a hydrogenation catalyst to produce a hydrogenation reaction product stream comprising THF, n-butyl alcohol (NBA) and/or 1,4-BDO and hydrogen;
    ii) separating the hydrogenation reaction product stream into a stream comprising THF, NBA and/or 1,4-BDO and a third gaseous stream comprising hydrogen; and
    iii) using at least a portion of said third gaseous stream comprising hydrogen as the first CO-lean gaseous stream.

* * * * *